(12) United States Patent
O'Donnell et al.

(10) Patent No.: US 12,193,944 B2
(45) Date of Patent: Jan. 14, 2025

(54) FUSION PLATE TO ASSIST FUSION OF A FIRST AND SECOND BONE

(71) Applicants: AA ENTERPRISES, LLC., Iowa City, IA (US); Turlough O'Donnell, Dublin (IE); Alan Laing, Dublin (IE); Annunziato Amendola, Iowa City, IA (US)

(72) Inventors: Turlough O'Donnell, Dublin (IE); Alan Laing, Dublin (IE); Annunziato Amendola, Iowa City, IA (US)

(73) Assignee: Arc Techtonics, Inc., Hampton, NH (US)

( * ) Notice: Subject to any disclaimer, the term of this patent is extended or adjusted under 35 U.S.C. 154(b) by 0 days.

(21) Appl. No.: 18/573,890

(22) PCT Filed: Oct. 5, 2022

(86) PCT No.: PCT/US2022/077606
§ 371 (c)(1),
(2) Date: Dec. 22, 2023

(87) PCT Pub. No.: WO2023/060122
PCT Pub. Date: Apr. 13, 2023

(65) Prior Publication Data
US 2024/0261111 A1   Aug. 8, 2024

(30) Foreign Application Priority Data
Oct. 5, 2021   (GB) .................................. 2114235

(51) Int. Cl.
*A61F 2/42*   (2006.01)
*A61B 17/80*   (2006.01)
*A61F 2/30*   (2006.01)

(52) U.S. Cl.
CPC ........ *A61F 2/4225* (2013.01); *A61B 17/8014* (2013.01); *A61B 17/8061* (2013.01);
(Continued)

(58) Field of Classification Search
CPC ............ A61B 17/8061; A61B 17/8076; A61B 17/8085; A61F 2/4225; A61F 2/4241
See application file for complete search history.

(56) References Cited

U.S. PATENT DOCUMENTS 7,635,365 B2   12/2009   Ellis et al.
8,906,070 B2   12/2014   Medoff
(Continued)

FOREIGN PATENT DOCUMENTS

CN   201234999 Y   5/2009
CN   202027696 U   11/2011
(Continued)

OTHER PUBLICATIONS

"International Search Report and Written Opinion received for PCT Patent Application No. PCT/EP2020/059817, mailed on Sep. 11, 2020", 14 pages.
(Continued)

*Primary Examiner* — Olivia C Chang
(74) *Attorney, Agent, or Firm* — Adler Pollock & Sheehan P.C.

(57) ABSTRACT

A fusion plate (1, 20) to assist fusion of a first bone (2) and second bone (3) comprising a rigid elongated plate configured to span the joint between the first and second bones having a C-shaped profile along its length, a thickness of 0.5 to 1.5 mm, and a plurality of holes (11) to receive bone-fixing screws (12) to fix the plate to the first and second bones, wherein the plurality of holes include at least one proximal hole disposed on each side (9, 10) of a proximal end (7) of the plate configured to receive proximal bone
(Continued)

fixing screws (12) in an orthogonal fixing screw configuration and at least one hole disposed on each side (9, 10) of a distal end (8) of the plate configured to receive distal bone fixing screws in an orthogonal fixing screw configuration. The plate may be configured for dorso-medial attachment and fusion of a meta-tarsal joint selected from a MetaTarsoPhalangeal joint (MTPJ) and a TarsoMetaTarsal Joint (TMTJ) of the big toe.

19 Claims, 9 Drawing Sheets

(52) U.S. Cl.
CPC .............. *A61F 2002/30131* (2013.01); *A61F 2002/30622* (2013.01); *A61F 2002/30777* (2013.01); *A61F 2002/4233* (2013.01); *A61F 2002/4238* (2013.01)

(56) References Cited

U.S. PATENT DOCUMENTS

| | | |
|---|---|---|
| 8,911,482 B2 | 12/2014 | Lee et al. |
| 8,998,904 B2 | 4/2015 | Zeetser et al. |
| 9,283,008 B2 | 3/2016 | Gonzalez-Hernandez |
| 9,333,014 B2 | 5/2016 | Gonzalez-Hernandez |
| 9,421,103 B2 | 8/2016 | Jeng et al. |
| 9,775,657 B2 | 10/2017 | Bernstein et al. |
| 9,877,754 B2 | 1/2018 | Patel et al. |
| 10,182,845 B2 | 1/2019 | Grant |
| 10,631,902 B2 | 4/2020 | Weiner et al. |
| 11,141,205 B2 | 10/2021 | Cox |
| 11,337,739 B2 | 5/2022 | Singh |
| 2005/0171544 A1 | 8/2005 | Falkner |
| 2007/0185493 A1 | 8/2007 | Feibel et al. |
| 2009/0210010 A1 | 8/2009 | Strnad et al. |
| 2009/0306724 A1 | 12/2009 | Leither et al. |
| 2009/0312759 A1 | 12/2009 | Ducharme et al. |
| 2010/0198266 A1 | 8/2010 | Nassab |
| 2010/0217328 A1 | 8/2010 | Terrill et al. |
| 2010/0256687 A1 | 10/2010 | Neufeld et al. |
| 2014/0107798 A1* | 4/2014 | Jeng .................... A61B 17/808 623/21.18 |
| 2014/0172020 A1 | 6/2014 | Gonzalez-Hernandez |
| 2014/0180344 A1 | 6/2014 | Gonzalez-Hernandez |
| 2014/0277176 A1 | 9/2014 | Buchanan et al. |
| 2015/0209093 A1 | 7/2015 | Dallis |
| 2015/0245858 A1 | 9/2015 | Weiner et al. |
| 2019/0059965 A1 | 2/2019 | Gausepohl et al. |
| 2019/0183549 A1 | 6/2019 | Singh |

FOREIGN PATENT DOCUMENTS

| | | |
|---|---|---|
| CN | 107320169 A | 11/2017 |
| CN | 207084848 U | 3/2018 |
| CN | 207561971 U | 7/2018 |
| CN | 108904031 A | 11/2018 |
| CN | 108926380 A | 12/2018 |
| CN | 208481441 U | 2/2019 |
| CN | 208784886 U | 4/2019 |
| CN | 109907810 A | 6/2019 |
| CN | 209136840 U | 7/2019 |
| CN | 209611280 U | 11/2019 |
| CN | 209884296 U | 1/2020 |
| CN | 209932949 U | 1/2020 |
| CN | 212816484 U | 3/2021 |
| CN | 212816485 U | 3/2021 |
| CN | 213075872 U | 4/2021 |
| FR | 3003749 A1 | 10/2014 |
| GB | 2435429 B | 3/2008 |
| JP | S5883954 A | 5/1983 |
| JP | 2011019710 A | 2/2011 |
| JP | 2012518467 A | 8/2012 |
| JP | 5728615 B1 | 6/2015 |
| JP | 2016104061 A | 6/2016 |
| WO | 2017207922 A1 | 12/2017 |
| WO | 2019126319 A1 | 6/2019 |
| WO | 2020201584 A1 | 10/2020 |
| WO | 2021175724 A1 | 9/2021 |
| WO | 2022086455 A1 | 4/2022 |

OTHER PUBLICATIONS

"International Search Report and Written Opinion received for PCT Patent Application No. PCT/US2022/077606, mailed on Jan. 13, 2023", 14 pages.

"Office Action received for GB Patent Application No. 2114235.1, mailed on Feb. 10, 2022", 4 pages.

"Office Action received for Japanese Patent Application No. 2021-560439, mailed on Dec. 26, 2023", 12 pages (6 pages of English Translation and 6 pages of Official Copy).

Acumed, "Clavicle Plating System", Product View, SHD00-04-B, 2021, 16 pages.

Depuy Synthes, "Foot & Ankle Product Portfolio", 2020, 8 pages.

Joeris, Alexander, et al., "The impact of the AO Foundation on Fracture Care: An Evaluation of 60 years AO Foundation", Injury, International Journal of the Care of the Injured, vol. 50, 2019, pp. 1868-1875.

Kitzen, et al., "Biomechanical Evaluation of Different Plate Configurations for Midshaft Clavicle Fracture Fixation : Single Plating Compared with Dual Mini-Fragment Plating. JBJS Open Access", JBJS Open Access, e21.00123, 2022, 8 pages.

Uhthoff, et al., "Internal Plate Fixation of Fractures: Short History and Recent Developments", Journal of Orthopaedic Science, vol. 11, 2006, pp. 118-126.

Zimmer Biomet, "A.L.P.S. Distal Tibis Plating System", Surgical Technique, 2021, 42 pages.

* cited by examiner

Right / Left

0°
10° dorsoflexion

FUSION PLATE TO ASSIST FUSION OF A FIRST AND SECOND BONE

FIELD OF THE INVENTION

The present invention relates to a fusion plate to assist fusion of a first and second bone. In particular, the invention relates to a fusion plate for bones of the foot, especially fusion of the MetaTarsoPhalangeal joint (MTPJ) and a TarsoMetaTarsal Joint (TMTJ) of the big toe.

BACKGROUND TO THE INVENTION

First (Big toe) MTPJ fusion is one of the most common procedures performed by foot and ankle surgeons to address osteoarthritis of the big toe (Hallux rigidus) or bunion deformity (Hallux valgus). A solid fusion, in a satisfactory position, is the ultimate goal and can offer pain relief, as well as excellent functional and aesthetic results, with few limitations. The achievement of a successful bony fusion requires surgical preparation of the joint surfaces to expose quality bone, appropriate alignment of the individual bones involved, with satisfactory contact between opposing surfaces, together with stable fixation for a critical period to permit bony healing/consolidation to occur. With successful bone healing the stabilizing construct (hardware) is no longer necessary, but in a majority of cases remains in situ, unless it causes soft tissue irritation.

Numerous techniques have been used to try and secure stable fixation, from wires to screws (headed and headless/threaded), plates, (locking or non-locking) or combined plate and screw configurations. Fusion remains the gold standard for end-stage big toe arthritis. Fusion is also widely used to address severe bunion deformity (hallux valgus) or where a bunion and arthritis co-exist.

To correct a severe valgus deformity, particularly where there is a large intermetatarsal angle, translation of the proximal phalanx may be necessary. This involves lateralizing the proximal phalanx and resecting the medial eminence. Contact between the opposing surfaces may be limited in this situation. This can make positioning of a lag or compression screw difficult or impossible and one may now be dependent on single plane stabilization with a dorsal plate. This may span a defect laterally, and with poorer stability, the risk of pull out or failure is greater.

Problems and deficiencies still exist with all fusion fixation devices due to the large leverage forces or torques generated at the joint and often, poor bone quality (osteopenia/osteoporosis). Increased stresses and limited suboptimal stability can create excessive motion at the fusion site resulting in non-union (where healing does not occur), hardware failure and revision surgery. Larger, bulkier (thicker) implants, always placed dorsally in an attempt to increase stiffness at the joint line, provide the stability necessary for bony healing to occur. These implants unfortunately still do not guarantee healing. They can be prominent, causing irritation to the skin and long extensor tendon, and irritation in closed shoes. Secondary extraction surgeries are often necessary to address these issues.

It is an objective of the invention to overcome at least one of the above-referenced problems.

SUMMARY OF THE INVENTION

The objective is met by the provision of a fusion plate having a low profile (e.g. 0.5 to 1.5 mm in thickness), a C-shaped profile to allow the plate wrap-around the ends of the bones being fused to provide multiplanar attachment to the each bone, and incorporates one or more holes at each side of each end of the plate that are sufficiently laterally spaced-apart to receive fixing screws in an orthogonal configuration. The C-shaped profile of the plate provides structural rigidity and torsional bending stiffness while maintaining a low profile. In addition, as the plate is pre-contoured, this obviates the requirement for a surgeon to have to modify the shape of the plate prior to attachment. The C-shaped profile also provide laterally opposed surface that are orthogonal (or nearly orthogonal) allowing fixing screws to be applied in or close to a 90°-90° configuration, which provides stable bone attachment on each side of the joint.

In a first aspect, the invention provides a fusion plate to assist fusion of a first and second bone comprising a rigid elongated plate configured to span the joint between the first and second bones having a C-shaped profile (typically along its full length), a thickness of 0.5 to 1.5 mm, and a plurality of holes to receive bone-fixing screws to fix the plate to the first and second bones, wherein the plurality of holes include at least one proximal hole disposed on each side of a proximal end of the plate configured to receive proximal bone fixing screws in an orthogonal fixing screw configuration and at least one hole disposed on each side of a distal end of the plate configured to receive distal bone fixing screws in an orthogonal fixing screw configuration.

In any embodiment, the fusion plate has a C-shaped profile at dorsal and medial sides of the elongated plate.

In any embodiment, the fusion plate has a C-shaped profile along its length.

In any embodiment, the fusion plate has a C-shaped profile along its full length.

In any embodiment, the first and second bones define a meta-tarsal joint of the foot in a subject. In another embodiment, the first and second bones define an ankle joint in a subject.

In any embodiment, the fusion plate is configured for fusion of a meta-tarsal joint selected from a MetaTarsoPhalangeal joint (MTPJ) and a TarsoMetaTarsal Joint (TMTJ) of the big toe.

In any embodiment, the fusion plate comprises at least three proximal holes disposed on the proximal end of the plate and at least three distal holes disposed on a distal end of the plate (e.g. two holes on one side and one hole on an opposite side of each end of the plate).

In any embodiment, the proximal holes are longitudinally staggered along the proximal end of the plate and the distal holes are longitudinally staggered along the distal end of the plate.

In any embodiment, the plate comprises a hemi-spherical arc shaped profile.

In any embodiment, the plate comprises a curved central section and flat lateral sections. In any embodiment, some or all of the screw-receiving holes are disposed in a periphery of the curved central section. In any embodiment, some or all of the screw-receiving holes are disposed in the flat lateral sections.

In any embodiment, the fusion plate is contoured and dimensioned for dorso-medial attachment to the first and second bones.

In any embodiment, a longitudinal axis of the plate is linear.

In any embodiment, a longitudinal axis of the plate is cranked dorsally towards a distal end thereof for example by up to 15°, preferably 4°-11°.

In any embodiment, at least two of the proximal holes and/or distal holes are configured to receive fixing screws in a 90°-90° fixing screw configuration.

In any embodiment, the fusion plate further comprises a bridging intermediate section between the proximal and distal ends.

In any embodiment, the intermediate section comprises an articulatable joint so that the fusion plate can be flexed about the articulatable joint.

In any embodiment, the fusion plate further comprises a grafting access window.

In any embodiment, the grafting access window is defined in the medial side of the fusion plate between the proximal end and the distal end.

In any embodiment, the grafting access window has a generally inverted U-shape.

In any embodiment, the fusion plate further comprises a compression mechanism for compressing first and second bones in a longitudinal direction.

In any embodiment, the compression mechanism comprises an elongate compression slot for receiving a screw on the dorsal side of the proximal end of the plate.

In any embodiment, the compression mechanism further comprises an interfragmentary screw hole for receiving an interfragmentary screw on the distal end of the plate.

In any embodiment, the interfragmentary screw hole is located in a guide channel defined in the dorsal side of the proximal end.

In any embodiment, the guide channel is formed by an inclined open bore-like extrusion formed in the dorsal side.

In any embodiment, the plate has a length of 3-6 cm or 3-5 cm.

In any embodiment, the plate has a thickness of 0.5 to 1.5 mm or 0.75 to 1.24 mm.

In any embodiment, the holes in the plate are countersunk holes.

In any embodiment, the fusion plate is a monoblock.

In another aspect, the invention provides a kit comprising a plate of the invention and a plurality of bone-fixing screws.

In any embodiment, the kit comprises a plurality of fusion plates of the invention, including fusion plates of different sizes or different dorsoflexion.

In any embodiment, the screw receiving holes and screws are threaded to allow a screw to engage a hole in a threaded engagement.

The screws are generally dimensioned to extend into and across at least 50%, 60%, 70% or 80% of the target bone.

The screws may be one or more compression screws.

In another aspect, the invention provides a method of fusing a first bone and second bone together in an end-to-end arrangement in a subject in need thereof, comprising the steps of:
  providing a fusion plate of the invention;
  adjusting one or both of the bones into a desired fusion orientation;
  fixing a proximal end of the fusion plate to the first bone with at least two proximal fixing screws;
  fixing a distal end of the fusion plate to the second bone with at least two distal fixing screws;
  wherein the proximal fixing screws engage the first bone in an orthogonal configuration and the distal fixing screws engage the second bone in an orthogonal configuration In any embodiment, the first and second bones are bones of the foot.

In any embodiment, the first and second bones define a joint selected from a MetaTarsoPhalangeal joint (MTPJ) and a TarsoMetaTarsal Joint (TMTJ) of the big toe.

In any embodiment, the method comprises fixing the fusion plate to the bones in a dorsal-medial orientation in which the proximal end of the plate is fixed to a dorsal surface of the first bone by at least one proximal fixing screw and is fixed to a medial surface of the first bone by at least one proximal fixing screw, and the distal end of the plate is fixed to a dorsal surface of the second bone by at least one distal fixing screw and is fixed to a medial surface of the second bone by at least one distal fixing screw, In any embodiment, the method comprises a step of resection of an end of one or both bones prior to fixing the fusion plate to the bones.

In any embodiment, the method is a method of MetaTarsoPhalangeal joint (MTPJ) or TarsoMetaTarsal Joint (TMTJ) fusion in a subject.

In any embodiment, the subject has a valgus deviation in the MPTJ.

In any embodiment, the method comprises one or both of resection of the prominent medial eminence and lateralizing the proximal phalanx prior to fixing the fusion plate to the bones.

In any embodiment, the subject has osteoarthritis of the big toe.

In any embodiment, the method comprises a step of adjusting the first and second bones into a dorsoflexion orientation and fixing the plate to the bones, wherein a longitudinal axis of the plate is cranked dorsally towards a distal end thereof.

In any embodiment, the plate is cranked dorsally by 5° to 10°.

The plate of the invention is an orthopaedic implant, generally comprising a plate and screw construct, designed specifically for stabilization of a big toe/first MTPJ fusion.

In any embodiment, the method further includes the step of placing a bone graft between the bones after fixing the fusion plate to the bones.

The C cross-section and wrap around configuration implies that the plate is reinforced along a central axis which can resist greater bending moments than conventional uniplanar plates.

The plate may be configured to be applied dorso-medially to resist the bending lever/torque at the first MTPJ. The sagittal component of the plate significantly increases the bending resistance, conferring stability.

The plate of the invention offers multiplanar fixation.

Screw hole orientation on the plate allows for a 90-90 degree locking screw configuration.

Lag screws may complement the construct, but are not necessary where good bone contact is secured.

The plate of the invention is pre-contoured to be straight or offer up to 10 degrees of dorsiflexion.

The plate of the invention is low profile (0.5 to 1.5 mm), which reduces soft tissue and extensor tendon irritation, and obviates the need for removal.

Other aspects and preferred embodiments of the invention are defined and described in the other claims set out below.

DETAILED DESCRIPTION OF THE INVENTION

Figure 1:
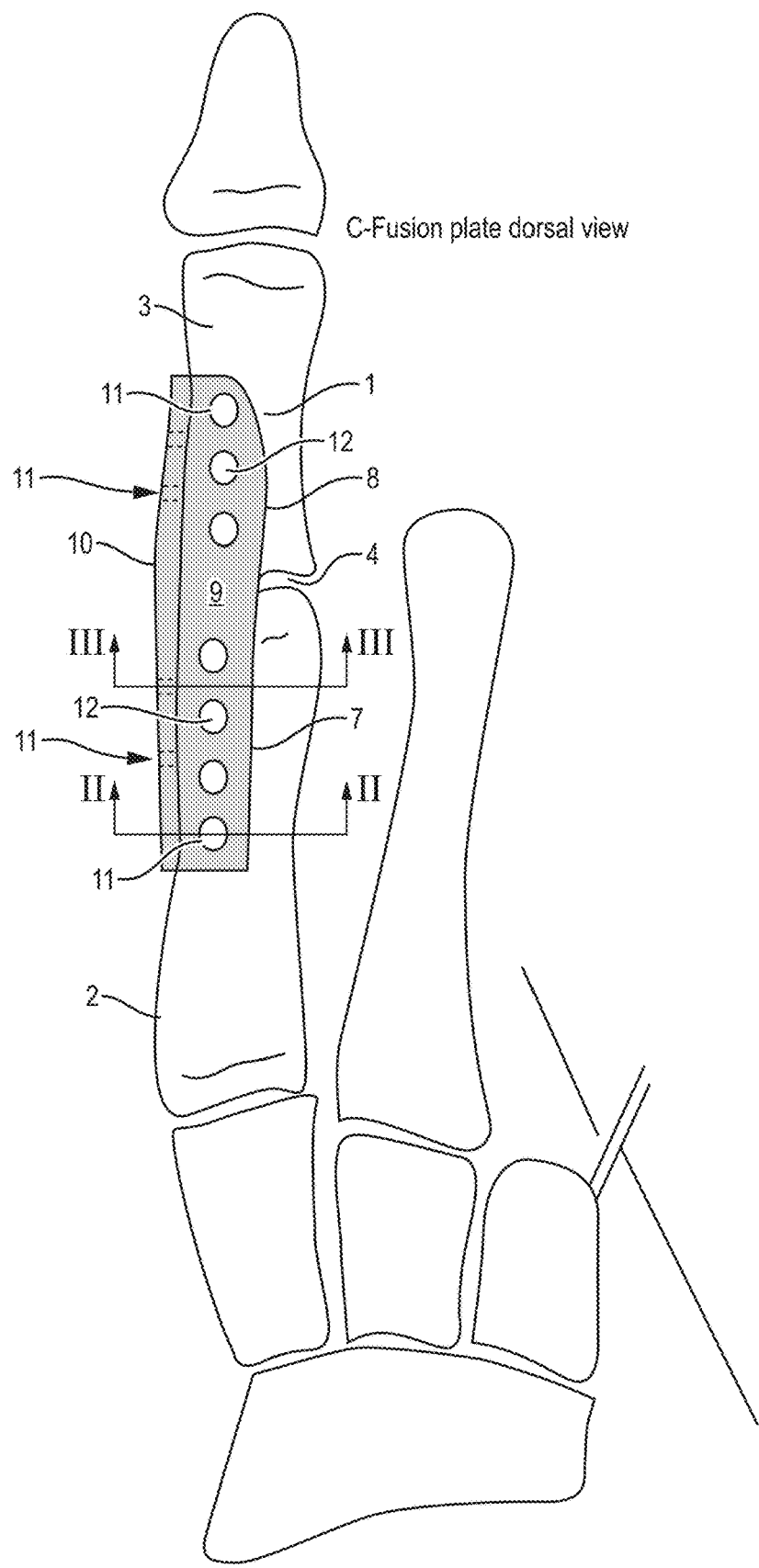
FIG. 1 is a dorsal view of a first embodiment of a meta-tarsal joint fusion plate of the invention attached to a MetaTarsoPhalangeal joint (MTPJ) of a big toe of a right foot of a subject.

All publications, patents, patent applications and other references mentioned herein are hereby incorporated by reference in their entireties for all purposes as if each individual publication, patent or patent application were specifically and individually indicated to be incorporated by reference and the content thereof recited in full.

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "C-shaped profile" means that the plate has a curved profile configured to curve around at least two surfaces of a bone, for example a dorsal and medial side/surface, and provides peripheral laterally-opposed surfaces for screw-receiving holes that are sufficiently laterally spaced apart across the plate to allow fixing screws fix the plate to the bone at or close to an orthogonal configuration (for example the screws may be at 80° to 100° to each other when fixed to the bone, but preferably are disposed at a 90°-90° orientation. The C-shaped profile can extend along the full length of the fusion plate and particularly along the full length of the dorsal and medial sides. The C-shaped profile may be an arc shape configured to extend from 80° to 120° around a bone, 90° to 100°. The plate may include a hemi-spherical arc section. The plate may include lateral sections that are not curved in profile.

As used herein, the term "orthogonal fixing screw configuration" means that the at least two holes at each end of the plate are sufficiently laterally spaced apart such that the fixing screws engage the bone at or close to an orthogonal configuration (at about 80° to about 100°). Ideally the at least two holes are positioned to provide the fixing screws at a 90°-90° orientation.

As used herein, the term "monoblock" as applied to a plate means that the plate is formed in one piece, generally by casting or moulding. It is distinct from plates that are formed in multiple parts and assembled or contoured after formation.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Figure 2:
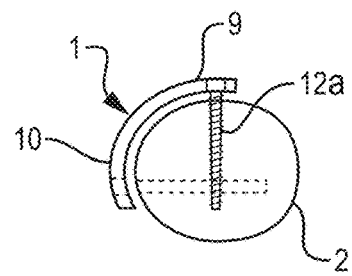
FIG. 2 is a section view taken along the lines II-II of FIG. 1 showing fixing screws attached to opposed sides of a proximal end of the plate that are slightly longitudinally staggered and disposed in a 90°-90° configuration for improved stability.
Figure 3:
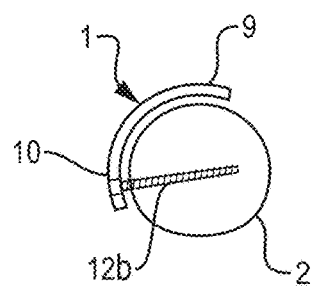
FIG. 3 is a sectional view taken along the lines III-III of FIG. 1.
Figure 4:
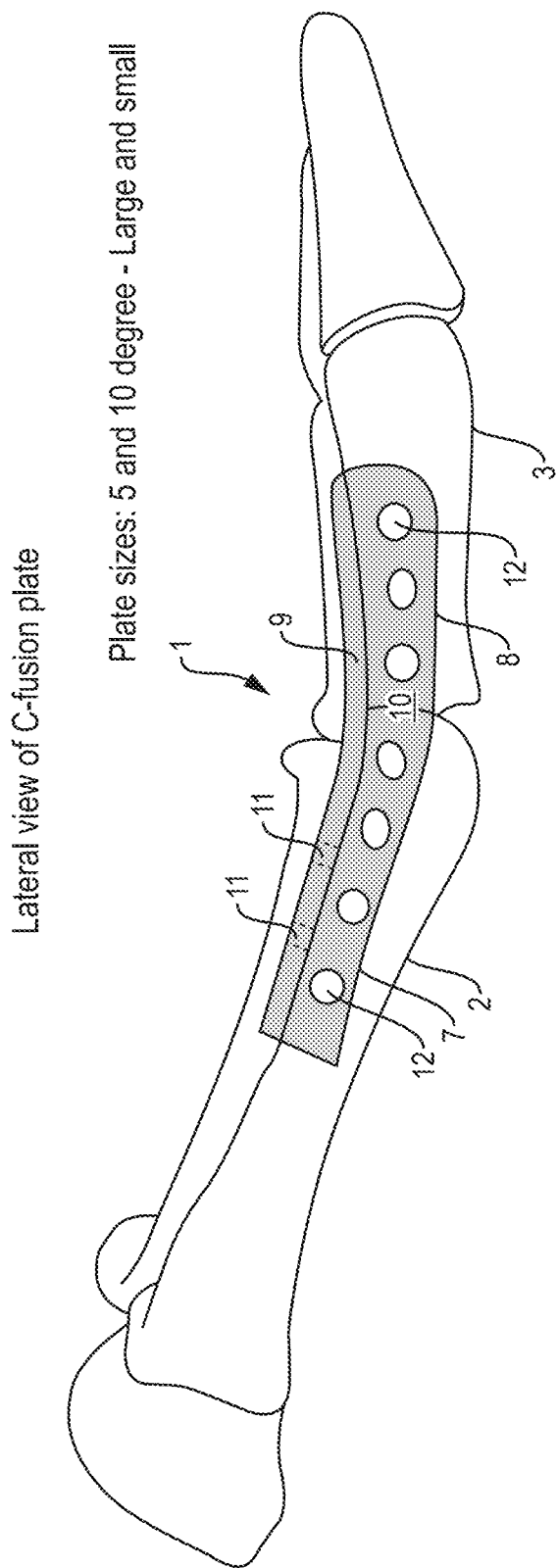
FIG. 4 is a medial view of a fusion plate of the invention attached to a MetaTarsoPhalangeal joint (MTPJ) of a big toe of a left foot of a subject.

Referring to the drawings, and initially to FIGS. 1 to 4, there is illustrated a fusion plate of the invention, indicated generally by the reference numeral 1, and in this case a fusion plate for MetaTarsoPhalangeal joint (MTPJ) of the big toe. The plate 1 is shown attached to a first bone (metatarsal) 2 and a second bone (proximal phalanx) 3 and spanning the MTPJ 4. The plate has a thickness of 1 mm and a length of 4 cm and comprises a proximal end 7, distal end 8, and a C-shaped cross-sectional profile along its length providing a dorsal side or surface 9 and medial side or surface 10. Holes 11 for fixing screws 12 are provided along the dorsal surface 9 of the plate (FIG. 1) and along the medial surface 10 of the plate (FIG. 4). The C-shaped profile of the plate allows the holes on the dorsal and medial sides 9,10 of the plate 1 to be sufficiently laterally spaced apart such that when fixing screws 12 are applied to fix the plate 1 to the bone, the screws on each side 9,10 of the plate 1 engage the bone at approximately 90° to each other. This provides significant stability. In addition, the dorsal and medial holes 11 are longitudinally staggered, which allows the use of screws 12 that extend almost fully into and across the bone. This is illustrated in the sectional views of FIGS. 2 and 3 which show a sectional view of the fusion plate in-situ and a fixing screw 12A attaching the dorsal surface 9 of the plate 1 to the dorsal surface of the metatarsal (FIG. 2) and a fixing screw 12B attaching the medial surface 10 of the plate 1 to the medial surface of the metatarsal. The holes 11 on the dorsal and medial surface 9,10 of the plate 1 do not need to be staggered, but providing staggered holes 11 allows the use of screws 12 that are sufficiently long to extend into across most of the bone.

The plate of FIGS. 1 to 3 is shown attached to a Meta-TarsoPhalangeal joint (MTPJ) of the big toe of a right foot, and in FIG. 4 it is shown attached to the same joint of a left foot. In this embodiment, the fusion plate 1 is cranked intermediate its ends by about 10°, providing for 10° of dorsoflexion. The plate 1 does not have to be cranked, and may be neutral or provide a different degree of dorsoflexion, depending on the patient. Generally, a surgeon will know in advance of the surgery whether a dorsoflexion fusion plate 1 is required, and the degree of dorsoflexion that is required.

In the embodiment shown, the fusion plate 1 has seven dorsal holes 11 and seven proximal holes 11, but it will be appreciated that fewer holes 11 may be required depending on the joint being treated and the health of the joint. Generally each end of the plate 1 requires at least two or three holes 11, including at least one on each laterally opposed surface of the plate 1.

Figure 5:
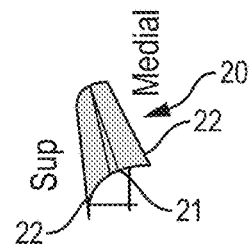
FIG. 5 is a perspective view of a fusion plate according to an embodiment of the invention.

FIG. 5 shows a perspective view of a fusion plate 20 according to the invention showing the C-shaped profile of the plate and a central hemi-spherical section 21 and lateral flat sections 22.

Figure 6:
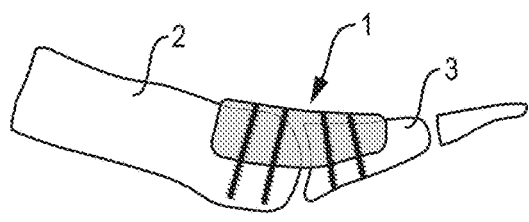
FIG. 6 is a medial view of a fusion plate of the invention having 10° dorsoflexion attached to a MetaTarsoPhalangeal joint (MTPJ) of a big toe of a left foot of a subject.
Figure 7:
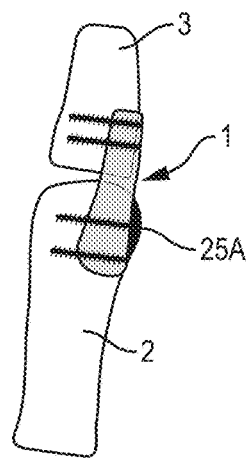
FIG. 7 is a dorsal view of a fusion plate of the invention attached to a MetaTarsoPhalangeal joint (MTPJ) of a big toe of a left foot of a subject in which part of the medial eminence of the metatarsal has been resected.
Figure 8:
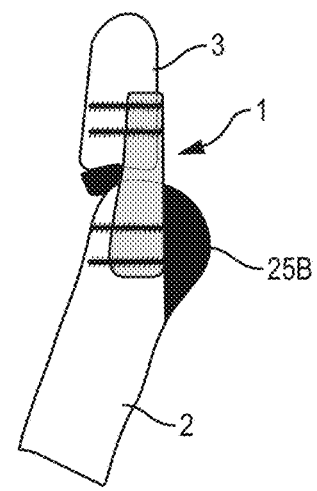
FIG. 8 is a dorsal view of a fusion plate of the invention attached to a MetaTarsoPhalangeal joint (MTPJ) of a big toe of a left foot of a subject in which part of the medial eminence of the metatarsal has been resected.
Figure 9:
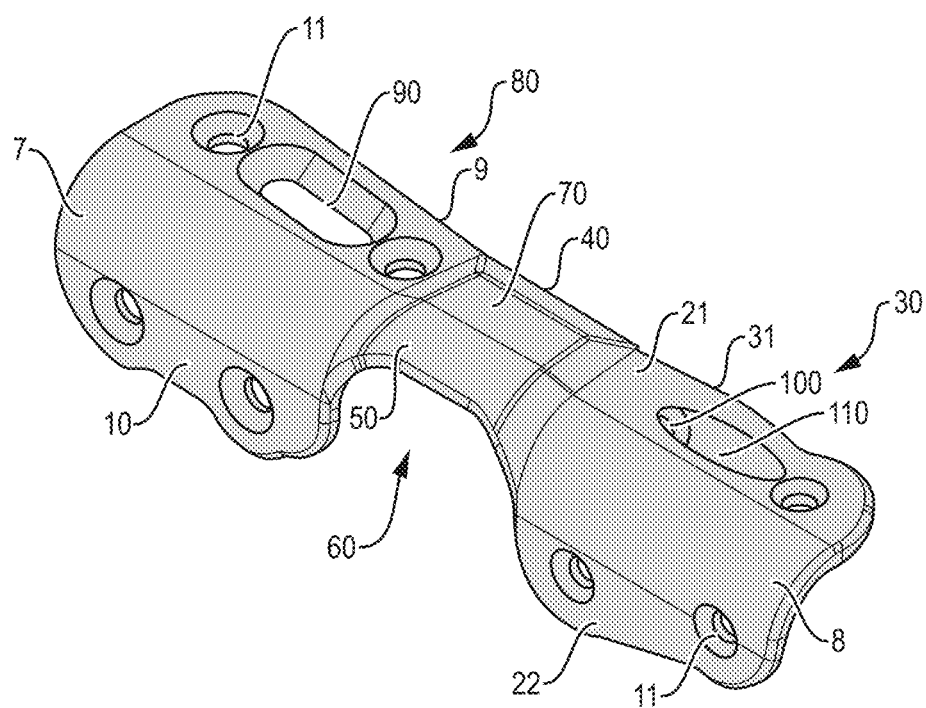
FIG. 9 is a perspective view from above and one side of a second embodiment of a meta-tarsal joint fusion plate of the invention in which the fusion plate has a bridging intermediate section between the proximal and distal ends for facilitating cranking or bending of the fusion plate and the fusion plate is configured to define a grafting recess or access window for facilitating post-fusion plate attachment bone grafting, a compression slot and associated interfragmentary screw hole.
Figure 10:
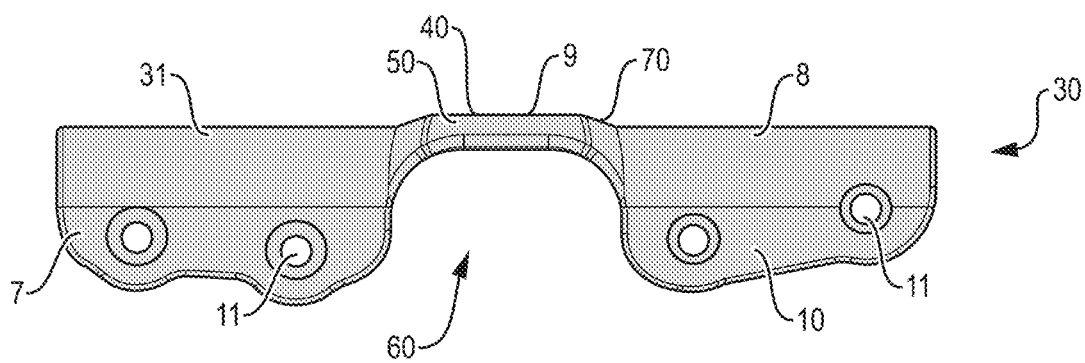
FIG. 10 is a medial view of the fusion plate.
Figure 11:
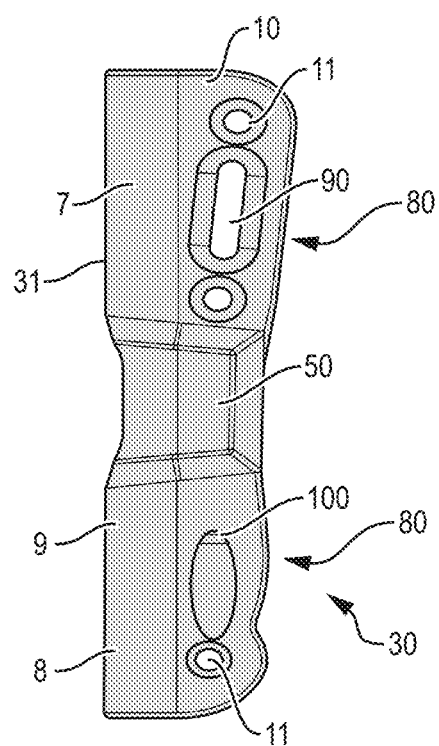
FIG. 11 is a top view of the fusion plate.
Figure 12:
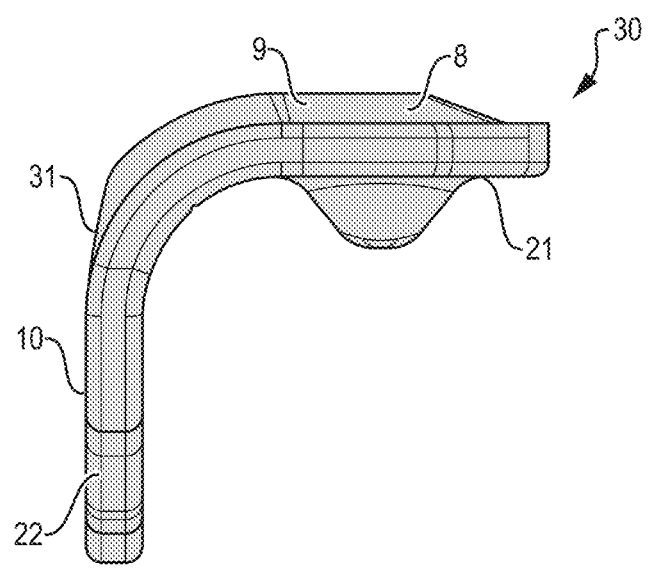
FIG. 12 is an end view of the fusion plate.
Figure 13:
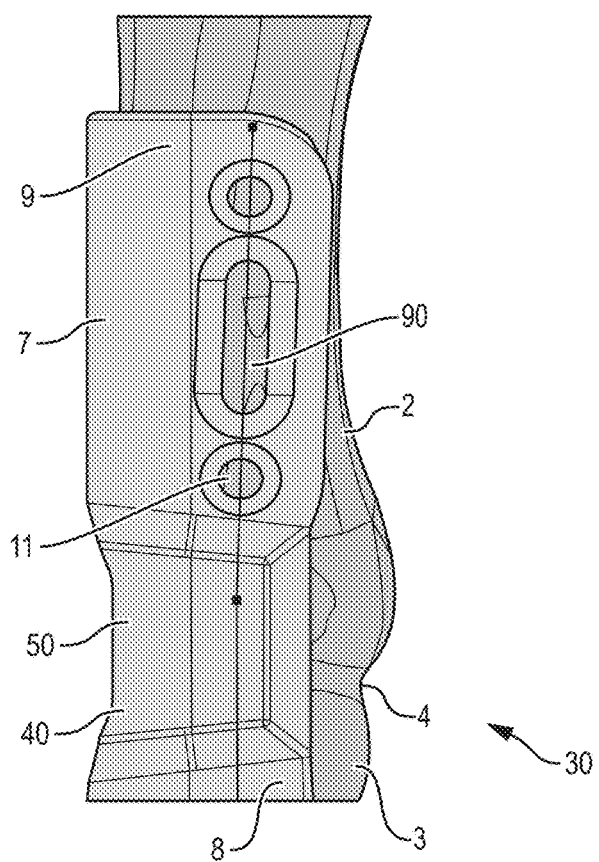
FIG. 13 is an enlarged top view of the compression slot of the fusion plate with the fusion plate attached to a metatarsal bone and a proximal phalanx and spanning the MTPJ joint.
Figure 14:
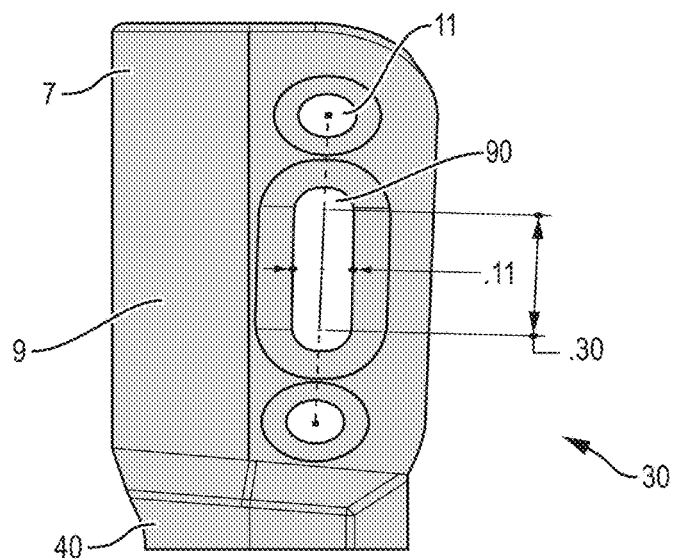
FIG. 14 is a further enlarged view of the compression slot showing the dimensions of the slot and the direction of toe geometry followed by the slot.

FIGS. 6 to 8 show the use of the plate to fuse a Meta-TarsoPhalangeal joint (MTPJ) of the big toe in patients with different clinical requirements. In FIG. 6, the plate has 10° of dorsoflexion. In FIGS. 7 and 10, the plate 20 is neutral (no dorsoflexion) and is affixed to bone that has been surgically resected due to the patient presenting with a bunion deformity (Hallux valgus). The bunion deformity in FIG. 7 is less severe, meaning that only a small part 25A of the medial eminence of the metatarsal has had to be resected, whereas in FIG. 8 a larger section of the medial eminence 25B has had to be resected. In both cases, resection is performed prior to the plating procedure, and the medial eminence is resected so as to conform to the shape of the proximal end of the C-shaped profile of the fusion plate.

FIGS. 9 to 21 show a third embodiment of a meta-tarsal joint fusion plate of the invention generally indicated by the reference numeral 30 which is broadly similar to the embodiments described in FIGS. 1 to 8 and like numerals indicate like parts. Accordingly, the fusion plate 30 is made up of an elongate plate 31 with a generally C-shaped cross-sectional profile having a proximal end 7 and a distal end 8 together defining a dorsal side 9 and a medial side 10. The C-shaped profile is pronounced at and particularly extends along the full length of the dorsal and medial sides 9,10 so that the fusion plate 30 effectively curves around at least two surfaces of a bone 2,3. The dorsal and medial sides 9,10 of the proximal and distal ends 7,8 are provided with holes 11 for receiving screws which have been omitted for clarity.

However, in the present embodiment, elongate plate 31 is shaped and contoured to define a bridging intermediate section 40 between the proximal end 7 and the distal end 8 at the location of the meta-tarsal joint 4. The intermediate section 40 is contiguous with the proximal end 7 and the distal end 8 and serves as an articulatable joint or bridge 50 between the proximal end 7 and the distal end 8 so that the fusion plate 30 can be cranked or flexed about the articulatable joint 50 as desired by a surgeon in accordance with dorsoflexional requirements.

The elongate plate 31 is further shaped and configured to define a grafting recess or access window 60 for facilitating post-fusion plate attachment bone grafting. In the present embodiment, the grafting access window 60 is located in the medial side 10 of the fusion plate 30 between the proximal end 7 and the distal end 8. More particularly, the grafting access window 60 is a three sided grafting access window 60 defined by the proximal end 7, the distal end 8 and the intermediate section 40 so that grafting access window 60 is positioned at the meta-tarsal joint 4 in use (see in particular FIGS. 13, 18 and 19). In the present embodiment, the articulatable bridge 50 is shaped to be raised or convex as indicated by the reference numeral 70 with respect to the elongate plate 31 so that the grafting access window has a generally inverted U-shape and the articulatable bridge 50 meets the proximal end 7 and the distal end 8 at angles of about 92°. The access window 60 also facilitates ease of access to and prevents obstruction of the bones 2,3 during hallux valgus fusion procedures.

Figure 15:
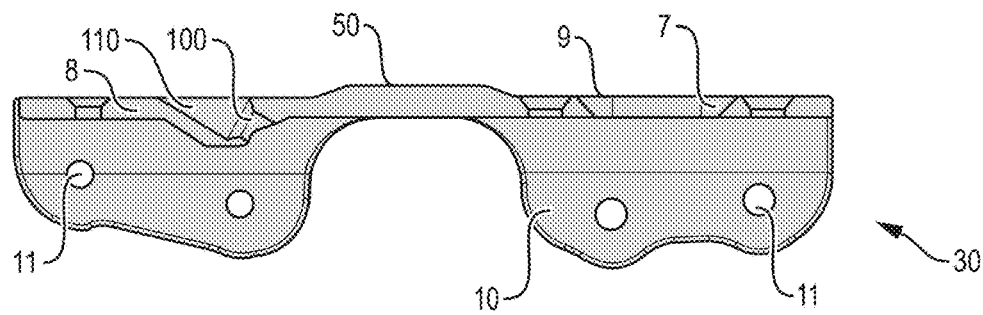
FIG. 15 is a longitudinal cross-sectional view through the fusion plate at the interfragmentary screw hole.
Figure 16:
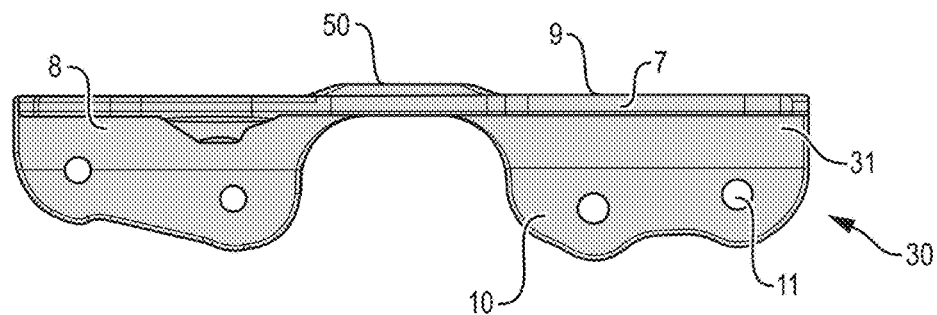
FIG. 16 is a further longitudinal cross-sectional view through the fusion plate adjacent the interfragmentary screw hole.
Figure 17:
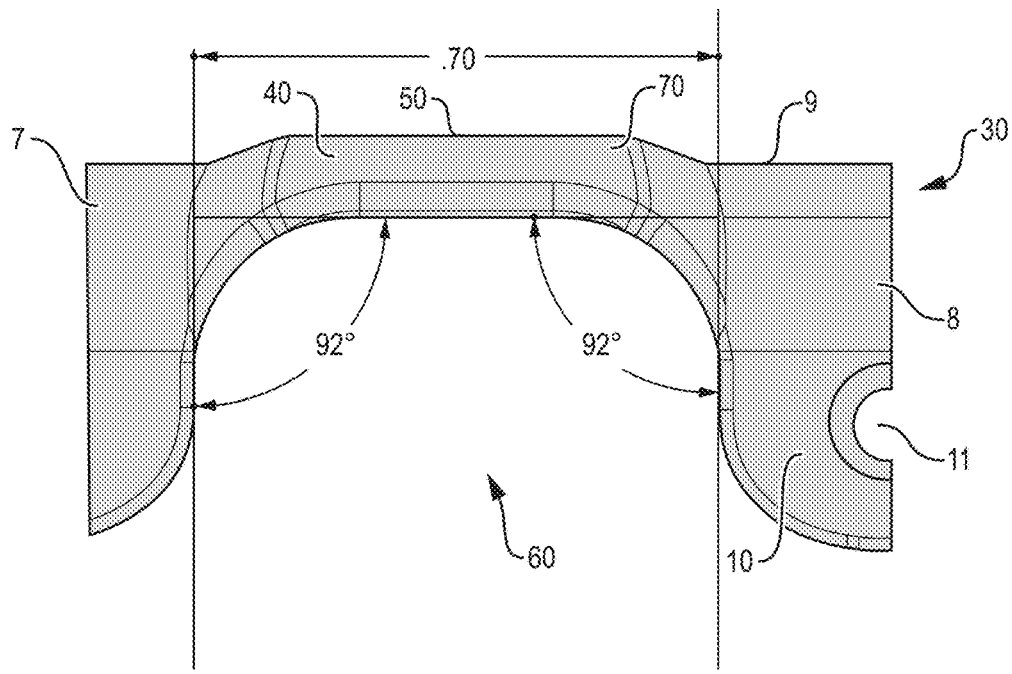
FIG. 17 is an enlarged medial view of the bone graft access window of the fusion plate.
Figure 18:
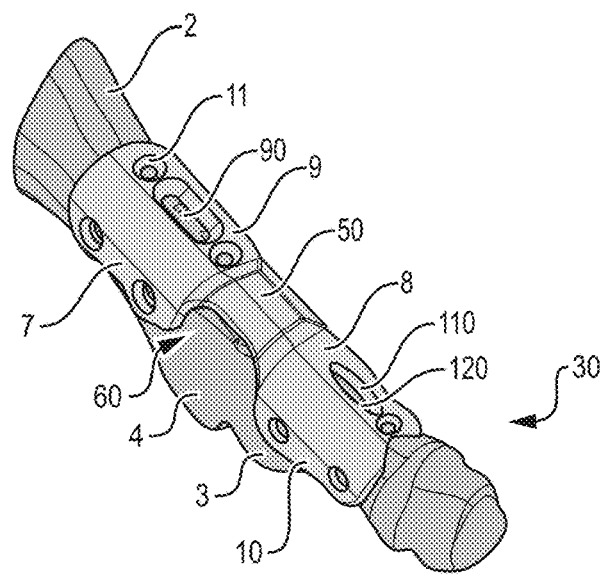
FIG. 18 is a perspective view from above and the access window side of the fusion plate attached to a MetaTarsoPhalangeal joint (MTPJ) of a big toe.
Figure 19:
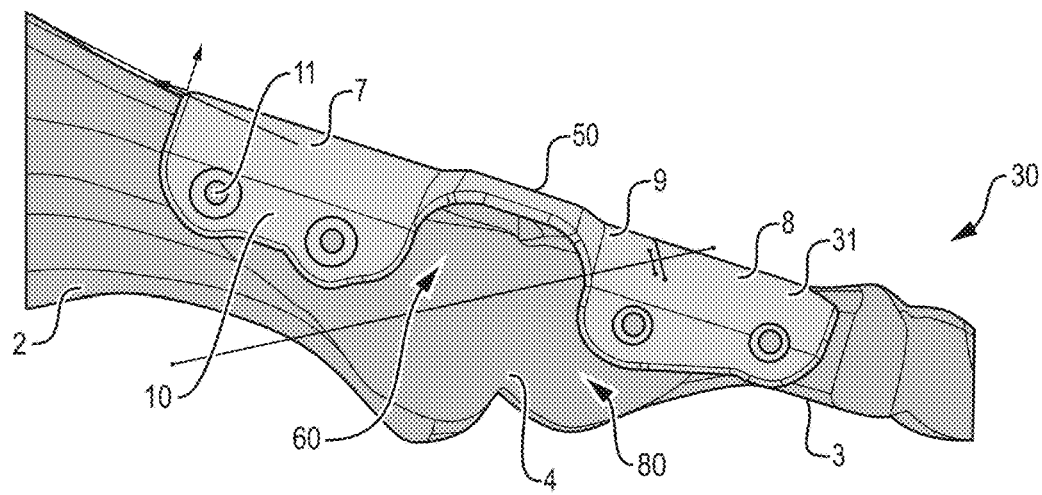
FIG. 19 is a medial perspective view of the fusion plate and joint of FIG. 18.
Figure 20:
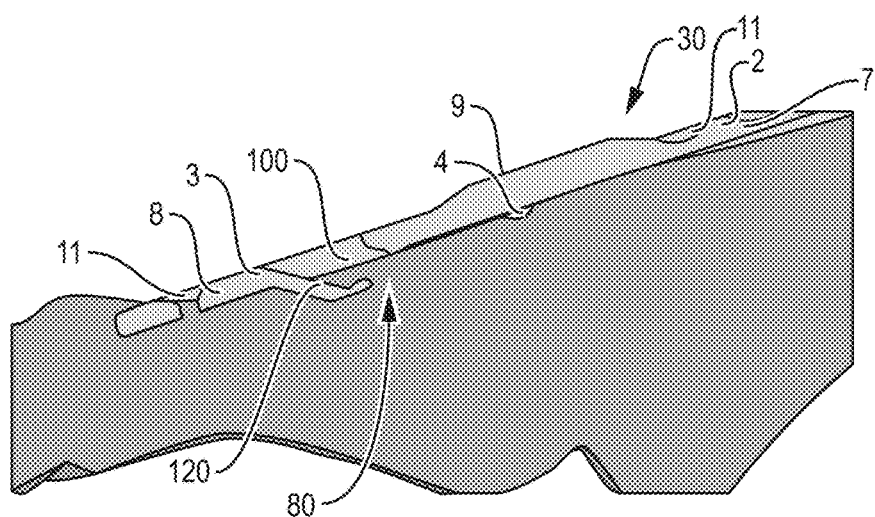
FIG. 20 is a cross-sectional view through the fusion plate and bone of the MetaTarsoPhalangeal joint (MTPJ) showing a portion of the bone having been removed to accommodate the interfragmentary screw hole extruded channel.
Figure 21:
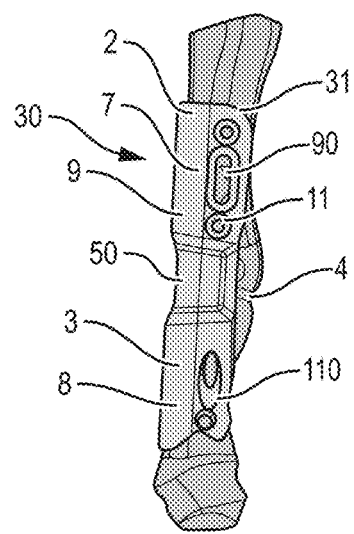
FIG. 21 is a top view of the fusion plate on the MetaTarsoPhalangeal joint (MTPJ).

The proximal end 7 of the fusion plate 30 of the invention is further provided with a compression mechanism 80 for compressing first and second bones 2,3 to be fused in a longitudinal direction (see in particular FIGS. 15, 19 and 20). In the present embodiment, the compression mechanism 80 is made up of an elongate compression slot 90 for receiving a screw on the dorsal side 9 of the proximal end 7 of the elongate plate 31 and an interfragmentary screw hole 100 for receiving an interfragmentary screw on the distal end 8 of the elongate plate 31. The interfragmentary screw hole 100 is located in a downwardly inclined guide channel 110 defined in the dorsal side 9 of the proximal end so that the interfragmentary screw is correctly guided into bone at an offset angle as shown particularly in FIG. 19. In the present embodiment, the guide channel 110 is formed by an inclined open bore-like extrusion 120 formed on the dorsal side 10.

In the present embodiment, the fusion plate 30 is described as being provided with the intermediate section 40, the grafting access window 60 and the compression mechanism 80. However, as will be appreciated by those skilled in the art, in other embodiments of the invention, the fusion plate 30 can be provided with these features singly or in any combination as required e.g. a fusion plate 30 with a compression mechanism 80 only, an intermediate section 40 only or a grafting access window 60 only or any combination of the aforementioned features as required.

In use, the fusion plate 30 is placed at a meta-tarsal joint 4 as previously described with the intermediate section 40 and the grafting access window 60 positioned at the meta-tarsal joint 4 as shown in the drawings. If required, the fusion plate 30 can be flexed as required by the surgeon about the articulatable bride 50 in accordance with the degree of dorsoflexion required. It should be noted that prior to placement of the fusion plate 30, it may be necessary to remove bone material from the second bone 3 to receive the extrusion 120.

Prior to fully tightening screws in the holes 11 on the proximal and distal ends 7,8 and a compression screw inserted through the compression slot 90, an interfragmentary screw is inserted through the guide channel 110 to extend between and compress the first and second bones 2,3 during which the compression screw can slide in the compression slot 90 in accordance with bone movement. The screws are then tightened to hold the fusion plate 30 in position.

If bone grafting (whether paste or segmental) is being performed, the dorsal and medial sides 9,10 hold the bones 2,3 in position while the bone graft can be placed between the bones 2,3 as required. Accordingly, in contradistinction with the prior art where bone graft must be placed between bones prior to placing a fusion plate at the joint, the access window 60 of the fusion plate 30 of the invention facilitates placement of the bone graft post-fusion plate attachment thus providing for a more anatomic graft and osteotomy.

While numerous orthopaedic plating systems exist for MTPJ fusion the fusion plate of the invention offers a number of unique features which confer an advantage over other plating techniques.
1. Greater stiffness in bending: The C-shaped profile of the fusion plate provides optimal fixation and bending resistance where bone contact and bone quality is suboptimal
2. Low profile: It is low profile (0.5-1.5 mm) which reduces soft tissue and extensor tendon irritation, and reduces the need for removal.
3. Multiplanar fixation: In poor quality bone, where compression/lag screw insertion is not achievable, the locking multi-axial fixation provides stability.
4. Severe valgus correction/stability where bone contact is limited: In the setting of hallux valgus correction, and an increased intermetatarsal angle, where the proximal phalanx is translated laterally the fusion plate of the invention can bridge areas of limited contact to offer stable fixation. The fusion plate of the invention offers low profile stabilization in orthogonal planes and provides contoured plates configured to wrap around the dorsal and medial surfaces of the opposing metatarsal and proximal phalanx during the correction of valgus deviation and resection of the prominent medial eminence. In brief the fusion plate of the invention permits translation of the proximal phalanx and stable fixation where bone contact is minimal. It also enables contouring or sculpting of the medial border to address medial prominence.
5. The fusion plate can be easily shaped as required through dorsoflexion.
6. Bone grafting can be performed through the bone graft access window thus providing for post-fusion plate attachment to provide for a more anatomic graft and osteotomy.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A fusion plate to assist fusion of a first bone and second bone comprising:
   a rigid elongated plate configured to span the joint between the first and second bones having a C-shaped profile, a thickness of 0.5 to 1.5 mm, and a plurality of holes to receive bone-fixing screws to fix the plate to the first and second bones, wherein the plurality of holes include at least one proximal hole disposed on each side of a proximal end of the plate configured to receive proximal bone fixing screws in an orthogonal fixing screw configuration and at least one hole disposed on each side of a distal end of the plate configured to receive distal bone fixing screws in an orthogonal fixing screw configuration;
   a compression mechanism for compressing first and second bones in a longitudinal direction;
   wherein the compression mechanism comprises an elongate compression slot for receiving a screw on the dorsal side of the proximal end of the plate;
   wherein the compression mechanism further comprises an interfragmentary screw hole for receiving an interfragmentary screw on the distal end of the plate; and
   wherein the interfragmentary screw hole is located in a guide channel defined in a dorsal side of the proximal end.

2. The fusion plate according to claim 1, in which the fusion plate has a C-shaped profile at a dorsal and medial side defined by the elongated plate.

3. The fusion plate according to claim 1, in which the fusion plate has a C-shaped profile along its length.

4. The fusion plate according to claim 1, in which the fusion plate has a C-shaped profile along its full length.

5. The fusion plate according to claim 1, in which the first and second bones define a meta-tarsal joint of the foot.

6. The fusion plate according to claim 5, configured for fusion of a meta-tarsal joint selected from a MetaTarsoPhalangeal joint (MTPJ) and a TarsoMetaTarsal Joint (TMTJ) of the big toe.

7. The fusion plate according to claim 1, including at least three proximal holes disposed on the proximal end of the plate and at least three distal holes disposed on a distal end of the plate.

8. The fusion plate according to claim 1, in which the proximal holes are longitudinally staggered along the proximal end of the plate and the distal holes are longitudinally staggered along the distal end of the plate.

9. The fusion plate according to claim 1, in which the plate has a hemi-spherical arc shaped profile.

10. The fusion plate according to claim 1, in which the fusion plate is contoured and dimensioned for dorso-medial attachment to the first and second bones.

11. The fusion plate according to claim 1, in which a longitudinal axis of the plate is linear.

12. The fusion plate according to claim 1, in which a longitudinal axis of the plate is cranked dorsally towards the distal end thereof.

13. The fusion plate according to claim 1, in which at least two of the proximal holes and/or distal holes are configured to receive fixing screws in a 90°-90° fixing screw configuration.

14. The fusion plate according to claim 1, further comprising a bridging intermediate section between the proximal and distal ends.

15. The fusion plate according to claim 1, wherein the intermediate section comprises an articulatable joint so that the fusion plate can be flexed about the articulatable joint.

16. The fusion plate according to claim 1, further comprising a grafting access window.

17. The fusion plate according to claim 16, wherein the grafting access window is defined in a medial side of the fusion plate between the proximal end and the distal end.

18. The fusion plate according to claim 17, wherein the grafting access window has a generally inverted U-shape.

19. The fusion plate according to claim 1, wherein the guide channel is formed by an inclined open bore-like extrusion formed in the dorsal side.

* * * * *